United States Patent [19]
Logue

[11] Patent Number: 5,793,204
[45] Date of Patent: Aug. 11, 1998

[54] METHOD OR GENERATING A ROTATING ELLIPTICAL SENSING PATTERN

[76] Inventor: Delmar L. Logue, R.R. #1, Box 60, Herrick, Ill. 62431

[21] Appl. No.: 599,775

[22] Filed: Feb. 12, 1996

Related U.S. Application Data

[63] Continuation-in-part of Ser. No. 142,933, Oct. 29, 1993, Pat. No. 5,532,591, Ser. No. 170,058, Dec. 20, 1993, abandoned, Ser. No. 187,072, Jan. 27, 1994, Pat. No. 5,574,367, Ser. No. 217,738, Mar. 25, 1994, Pat. No. 5,554,933, Ser. No. 388,825, Feb. 15, 1995, Pat. No. 5,548,212, and Ser. No. 416,971, Apr. 5, 1995, abandoned.

[51] Int. Cl.⁶ .............................. G01N 27/72; G01B 7/00; G06F 1/02; H03B 28/00
[52] U.S. Cl. .............. 324/228; 324/207.17; 324/207.26; 324/232; 324/239; 327/106
[58] Field of Search .................... 324/207.17, 207.25, 324/207.26, 228, 232, 239; 332/151, 173; 336/184, 195, 229; 364/718, 718.01–718.03; 327/105–107

[56] References Cited

U.S. PATENT DOCUMENTS

| | | | |
|---|---|---|---|
| 2,467,306 | 4/1949 | Habig | 324/242 |
| 4,379,261 | 4/1983 | Lakin | 324/232 X |
| 4,499,421 | 2/1985 | Sinclair | 324/232 X |
| 4,595,843 | 6/1986 | DelVecchio et al. | 336/184 X |
| 4,792,756 | 12/1988 | Lam et al. | 324/232 |
| 4,818,935 | 4/1989 | Takahashi et al. | 324/232 |
| 5,404,101 | 4/1995 | Logue | 324/207.17 |
| 5,508,607 | 4/1996 | Gibson | 324/121 R |

*Primary Examiner*—Gerard R. Strecker

[57] ABSTRACT

A method of increasing the spatial resolution of polar coordinates sensor devices by phase-amplitude modulating the sine-cosine excitation signals to the hollow toroid driving core. A rotating elliptical sensing pattern is generated by digital synthesis means. Values of the elliptical sensing pattern and its complete revolution are stored in digital "look-up" tables and sequentially read at a high rate into two digital-to-analog converters to produce two "staircase" approximations of the sine-cosine waveforms. The ellipse generation has a first angular frequency and the ellipse precession has a second sub-multiple frequency.

10 Claims, 7 Drawing Sheets

1

METHOD OR GENERATING A ROTATING ELLIPTICAL SENSING PATTERN

RELATED PATENT APPLICATIONS

This patent application is a continuation-in-part of patent applications:

Ser. No. 08/142,933 filed Oct. 29, 1993, U.S. Pat. No. 5,532,591;

Ser. No. 08/170,058 filed Dec. 20, 1993 (abandoned);

Ser. No. 08/187,072 filed Jan. 27, 1994, U.S. Pat. No. 5,574,367;

Ser. No. 08/217,738 filed Mar. 25, 1994, U.S. Pat. No. 5,554,933;

Ser. No. 08/388,825 filed Feb. 15, 1995, U.S. Pat. No. 5,548,212; and

Ser. No. 08/416,971 filed Apr. 5, 1995 (abandoned)

This invention was originally filed under the Disclosure Document Program as Disclosure Document No. 371371 Mar. 2, 1995.

THE INVENTION

The present invention relates to a method of increasing the spatial resolution of the proximity sensor disclosed in my parent U.S. Pat. No. 5,404,101 and also for increasing the resolving power of all the polar coordinates sensor devices disclosed in the above related pending patent applications.

In order to increase spatial resolution the polar coordinates sensing pattern is intentionly made elliptical shaped and the ellipse itself is rotated (precession). The ellipse generation (the induction vector drawing an individual ellipse) has a first angular frequency and the ellipse precession (also called coordinate rotation or coordinate system) has a second submultiple angular frequency.

This generated sensing pattern resembles a plurality of individual ellipses drawn at different angular positions (as in FIG. 6). The precession of individual ellipses generates the second submultiple angular frequency. The direction of the ellipse precession may be in the same direction as the ellipse generation or it may be in the opposite direction (counter-rotating) depending on the selected program.

The number of different sensing patterns that can be generated by suitable software ("look-up tables") is limited only by the steps contained in the program, some example program steps are listed below:

(1) The ellipse generation and the ellipse precession may rotate in the same direction (uni-directional).

(2) The ellipse generation and the ellipse precession may rotate in opposite directions (counter-rotational).

(3) The total number of individual ellipses (each having a different angular position) making up the sensing pattern are generated in one revolution.

(4) The total number of individual ellipses (each having a different angular position) making up the sensing pattern are generated by a plurality of revolutions.

(5) A predetermined number of individual ellipses may be generated in a positive direction (not necessarly a complete revolution) then a predetermined number generated in the negative direction but not necessarily at the former azimuth headings and not necessarly having the same azimuth range.

(6) The ellipse may precess to a predetermined azimuth heading and then a predetermined number of ellipses may be generated at that azimuth heading before advancing to the next azimuth heading.

(7) The degree of ellipse (minor elliptical axis) may be varied at any time in the program.

(8) Different clock frequencies may be selected.

(9) The ellipse generation frequency/ellipse precession ratio is variable, a circle may also be generated.

(10) Different combinations of the above program steps.

This unique sensing pattern is generated by unequal sine-cosine excitation magnitudes applied to the driving core. The azimuth sensing range is intentionally reduced on the minor elliptical axis to provide a degree of spatial differentiation.

The rotating elliptical pattern also subjects the workpiece to at least two induction frequencies, providing variable depth eddy currents in conducting materials for locating flaws.

This multi-frequency induction principle should be especially useful in detecting flaws in layered workpieces.

The rotating elliptical sensing pattern is generated by digital synthesis means. Values of the rotating elliptial sensing pattern and its complete revolution are stored in digital memory "look up tables". The look up tables are sequentially read at a high rate into two digital-to-analog converters ("DACS") which produce two "staircase" approximations of the amplitude modulated sine and cosine waveforms.

The digital memories (DACS) contain the resultant sine-cosine induction vector multiplied by a rotation matrix. This in effect amplitude modulates the sine-cosine excitation outputs to produce the rotating elliptical sensing pattern.

DETAILED DESCRIPTION OF THE INVENTION

Figure 1:
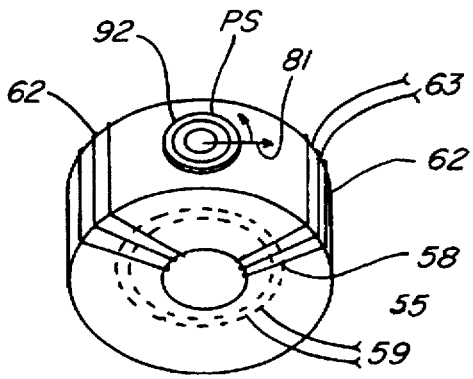
FIG. 1 is a perspective view of a polar coordinates sensor device including the driving core.

First to review the basics of polar coordinates sensing devices, refer now to FIG. 1, wherein there is shown in perspective view a hollow toroid core 55 formed of a high permeability material such as ferrite. The hollow toroid 55 has an inside excitation winding 58 wound within the hollow toroid driving core having connecting leads 59. Winding 58 can induce a first magnetic field throughout the entire core. There is an outside toroidal excitation winding 62, having connecting leads 63; this winding can induce a second magnetic field throughout the entire core. The inside and outside excitation windings are connected to a sine-cosine generator to induce a rotating magnetic field throughout the entire core. This type of rotating field was disclosed in the DelVecchio et al. U.S. Pat. No. 4,595,843.

Since the magnetic moments are the origin of rotation the driving field has distributive axes (plural) perpendicular to the surface of core 55 at all points. This rotating magnetic field may be utilized for eddy current sensing by mounting a polar sensor PS in a bore 92, in the outer circumference wall of the hollow toroid (see FIG. 3).

The axis of bore 92 is perpendicular to the central axis of the hollow toroid driving core 55, i.e. perpendicular to a plane drawn tangent to the surface of core 55.

Figure 2:
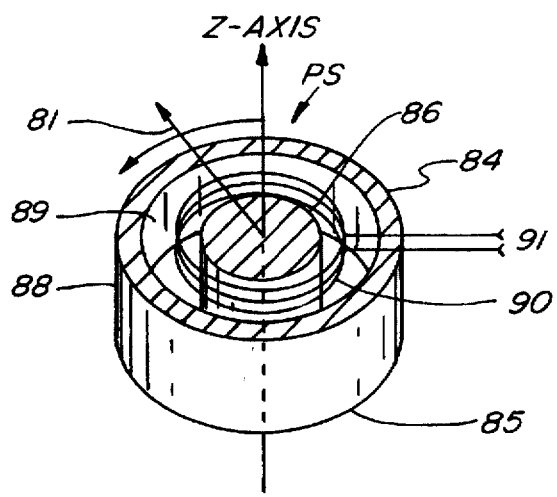
FIG. 2 is an isometric view of of a polar coordinates sensor without the driving core.

In this postion the pick-up coil 90 of FIG. 2 (polar sensor shown in enlarged detail) is disposed coplanar to the rotating flux lines crossing the mounted polar sensor PS. With no target present there is no flux coupling to the coplanar positioned pick-up coil, and a signal null is obtained.

Figure 3:
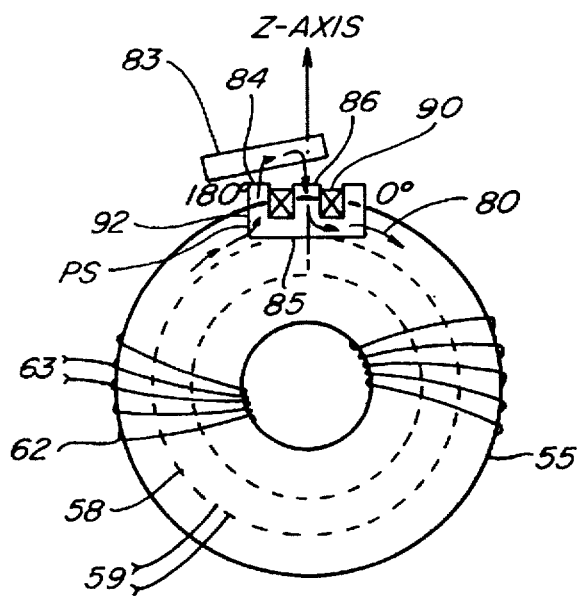
FIG. 3 is a radial view of the hollow toroid driving core and a cross-section view of the mounted polar coordinates sensor.

When a metallic target 83 (ferrous or non-ferrous) in FIG. 3 comes within the hemispherical sensing pattern the coplanar driving flux becomes unbalanced linking flux lines to pick-up coil 90 generating a signal. FIG. 2 is an isometric view of polar sensor PS showing the concentric construction. Pick-up core 88 comprises a central magnetic pole 86 concentrically surrounded by a cylindrical outer magnetic pole 84. The central and outer magnetic poles are concentrically spaced apart to provide an annular pick-up coil space 89. The aforementioned pick-up coil 90 is wound around the central magnetic pole 86, having connecting leads 91. The two magnetic poles and the pick-up coil share the same z-axis. Pick-up core 88 is formed of a high permeability ferromagnetic material such as ferrite, a conventional pot core half without lead slots was used in my prototype. The central and outer magnetic poles are connected by a base portion 85. The thickness of the base portion 85 is approximately ¼ the thickness of the the hollow toroid core wall. The mounted pick-up core 88 creates an annular shaped high reluctance in the hollow toroid wall. This annular shaped high reluctance provides the hemispherical fringing flux sensing pattern. The hemispherical sensing pattern is rotating coaxially with the z-axis of pick-up core 88. Pick-up core 88 is tightly mounted in bore 92 i.e. a good machined fit for uniform flux coupling. Referring to FIG. 3, a portion of pick-up core 88 is extending beyond the surface of the hollow toroid, this provides a more defined sensing pattern to the workpiece. The unsegmented outer cylindrical magnetic pole 84 provides a very uniform sensing pattern that allows near infinite angular resolution. Referring again to FIG. 3, the rotating induction vector within the hollow toroid driving core 55 forces flux lines 80 to flow up through the outer concentric magnetic pole 84, into the metal target (ferrous or non-ferrous) 83, down through the central magnetic pole 86, through the base portion 85, and back to the driving core 55 linking pick-up coil 90.

Figure 4:
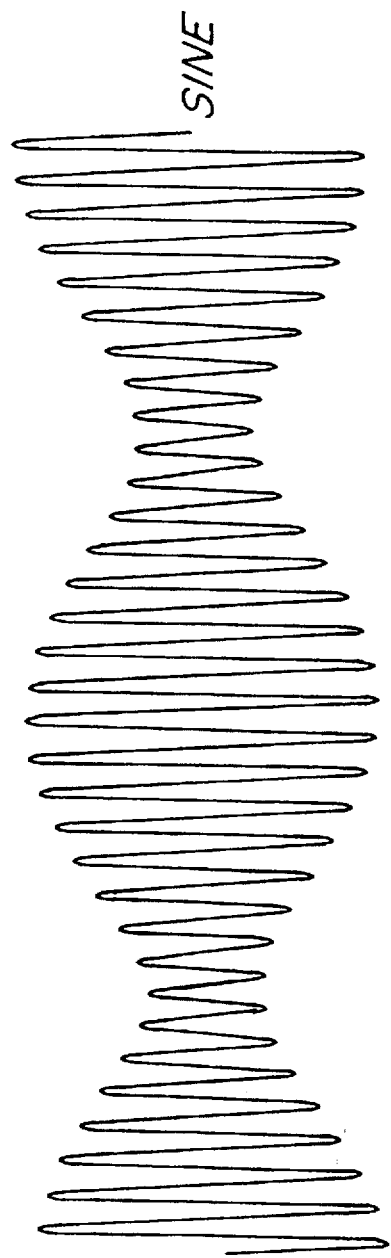
FIGS. 4 and 5 are the the two amplitude modulated sine-cosine excitation waveforms that generate the rotating elliptical sensing pattern.
Figure 5:
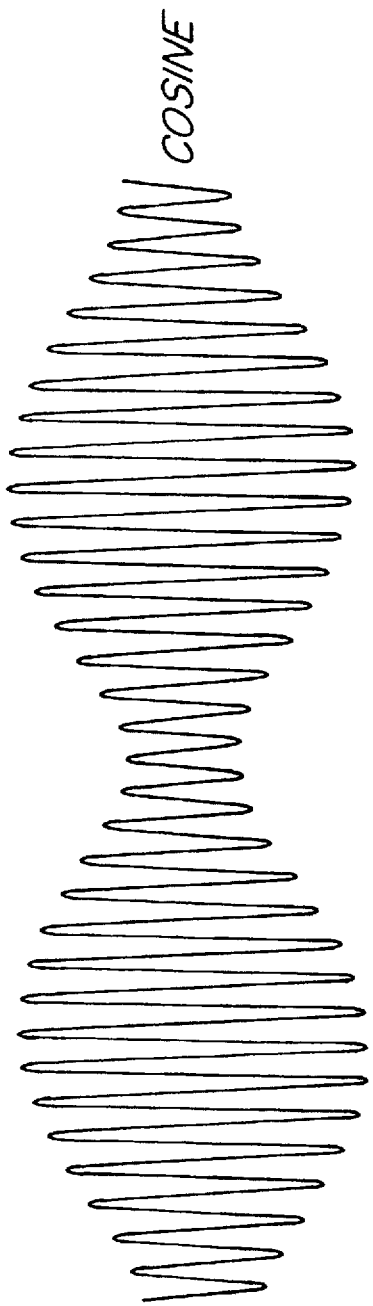
Figure 7:
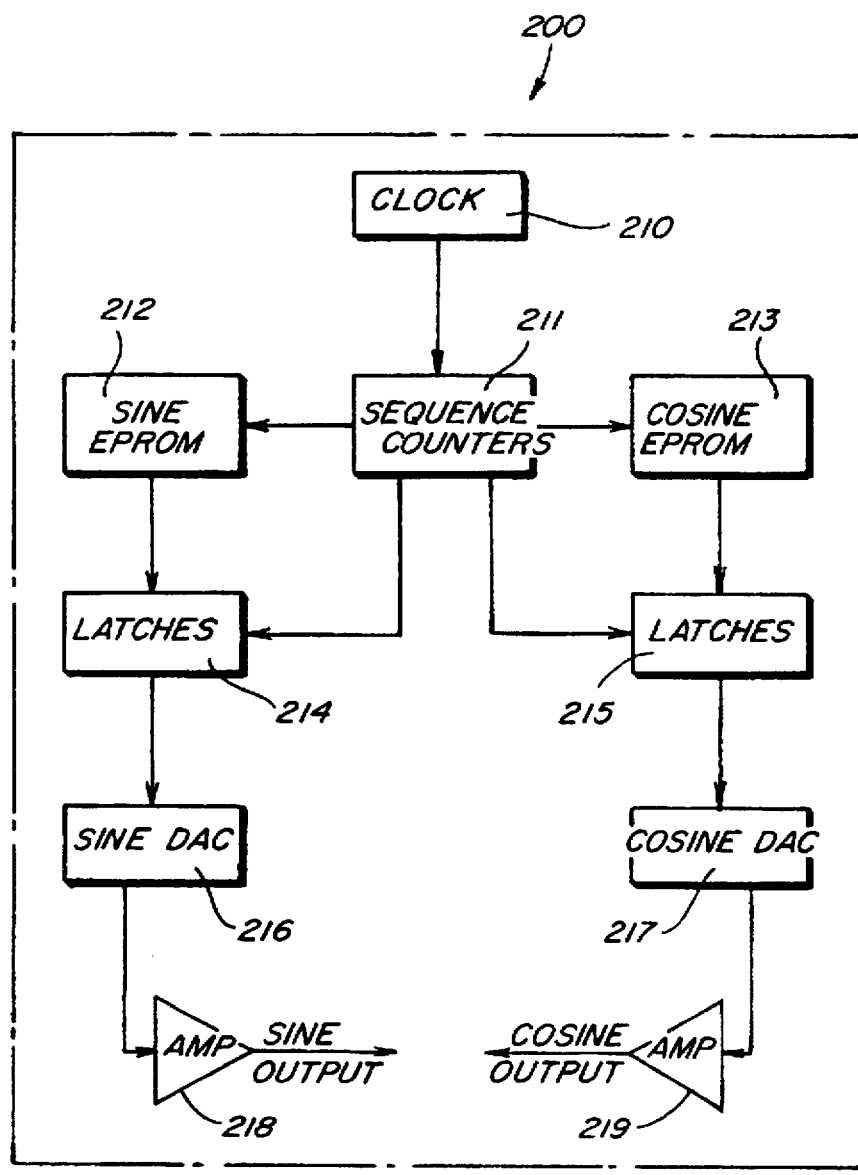
FIG. 7 is a block diagram of a digital sine-cosine generator for generating the two amplitude/phase modulated excitation waveforms that excite the driving core.

If the sine-cosine excitation magnitudes are equal and are 90 degrees out of phase, the resultant induction vector 81 in FIG. 1 (i.e. the vector sum of component induction vectors) rotates through 360 degrees. If the individual sinusoidal induction components of the resultant vector are of equal peak magnitude the rotating induction vector traces out a circle. The resultant induction vector also traces out an ellipse if the induction vectors have unequal amplitudes, or are not 90 electrical degrees apart (although spatially perpendicular in the hollow toroid core) both these modes of modulation may be utilized to create the rotating elliptical sensing pattern of the invention. The two excitation windings of the driving core are amplitude modulated according to FIGS. 4 and 5 to generate the rotating elliptical sensing pattern. FIGS. 4 and 5 are computer print-outs of the modulated sine-cosine outputs from the rotating elliptical pattern generator of FIG. 7 (a block diagram). The apparatus of FIG. 7 is a digital sine-cosine excitation generator 200 comprising a crystal controlled clock 210 driving a sequencer 211 made up of synchronous counters. The sequencer 211 drives sine eprom 212 and cosine eprom 213 in which are stored the values of the waveforms to be synthesized. The sequencer cycle must be an integer multiple of the number of sampled points contained in the eproms. The outputs of the eproms are fed into latches 214, 215, to ensure valid data while the eprom outputs are changing. Latches 214 and 215 drive two digital-to-analog converters 216, 217, which generate the analog sine and cosine signals. The sine and cosine signals are fed to two power amplifiers 218, 219, which supply current to the driving core.

Figure 6:
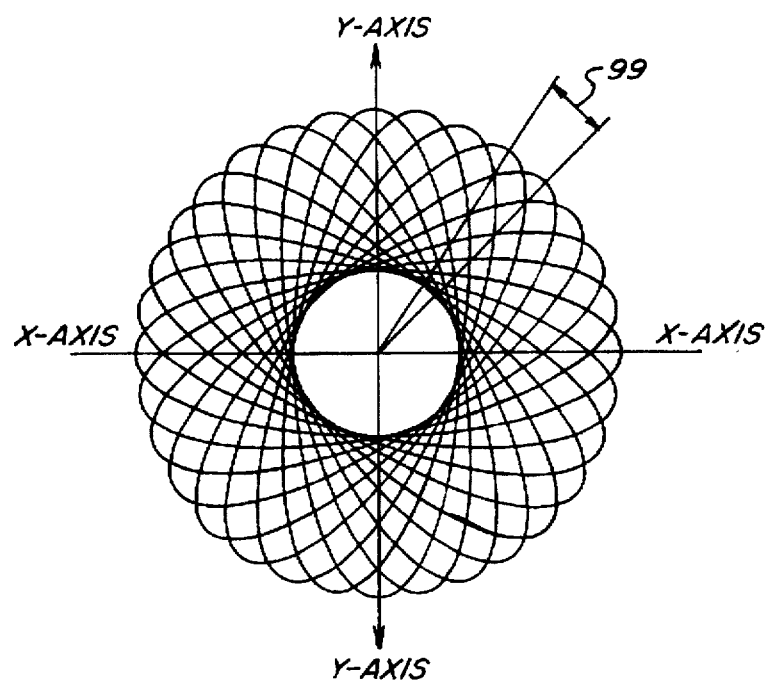
FIG. 6 is a computer generated figure of the excitation waveforms of FIGS. 4, 5 plotted on x-y axes.
Figure 8:
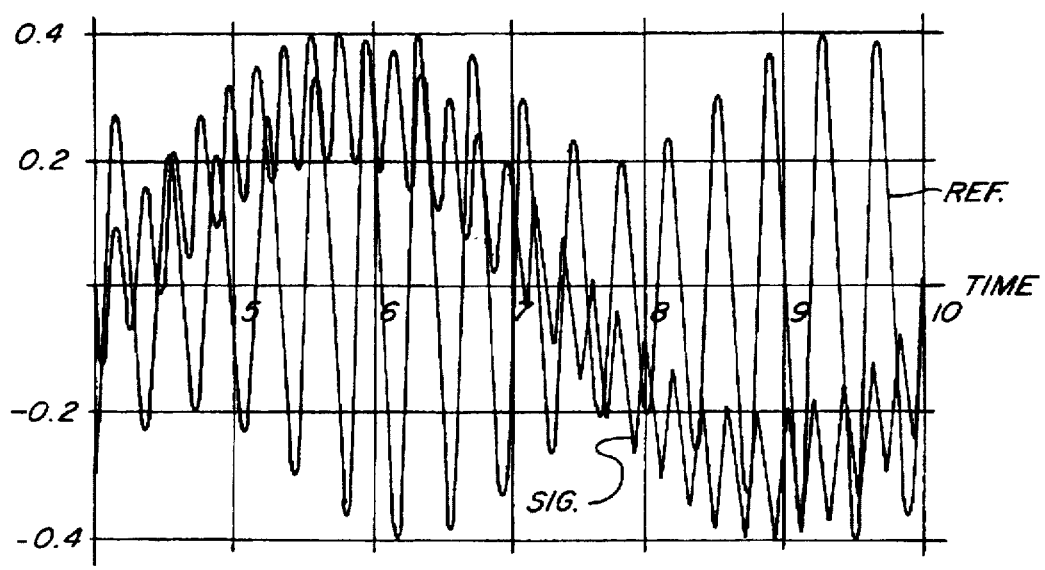
FIG. 8 is a graphical plot of the rotating elliptical signal.

The sine cosine excitation signals are plotted on x-y axes in FIG. 6 (a computer generated figure). The ellipse precession angle 99 is drawn on the major elliptical axis. It is contemplated the degree of ellipse may be made variable over a wide range by suitable software. This would change the amplitude ratio of the high/low frequency components in the output signal. This might be done as a linear change or an incremental change. FIG. 8 is an x-y graphical plot of the rotating elliptical signal (SIG.) shown along with one of the exciting signals REF. Analysing FIG. 8 we see there are two signal components i.e. a first angular frequency (ellipse generation) superimposed on top of a second angular submultiple frequency (the ellipse precession frequency, also called coordinate rotation). It is to be understood, the means (hardware and software) to modulate the two sine-cosine excitation waveforms is not limited to the example circuit of FIG. 7 as many other circuits and programs are possible.

Figure 9:
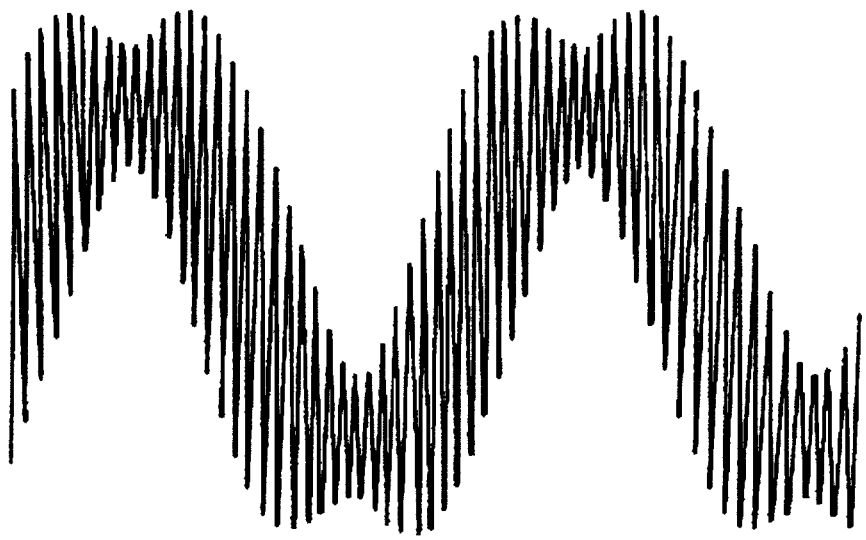
FIGS. 9 and 10 are oscilloscope pictures of the rotating elliptical signal.
Figure 10:
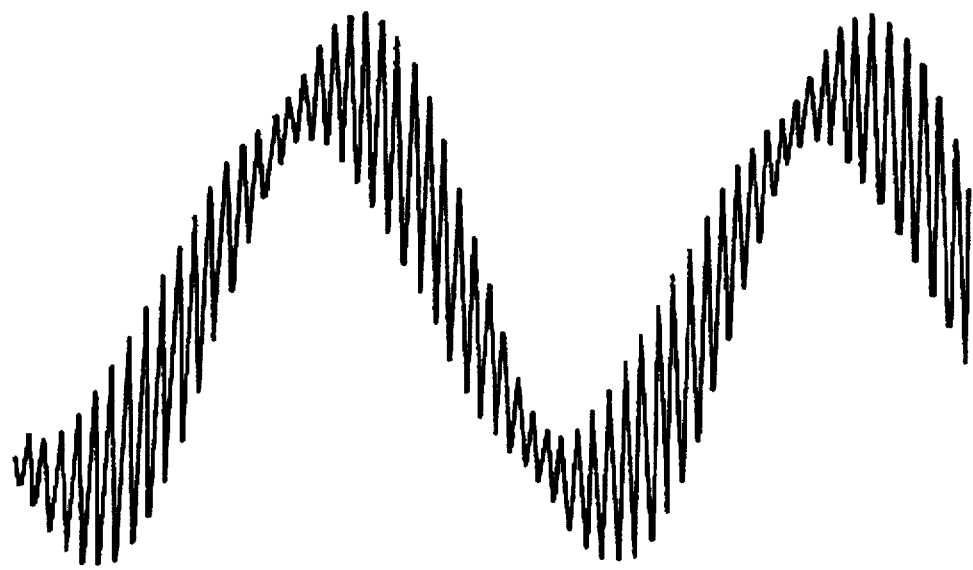
Figure 11:
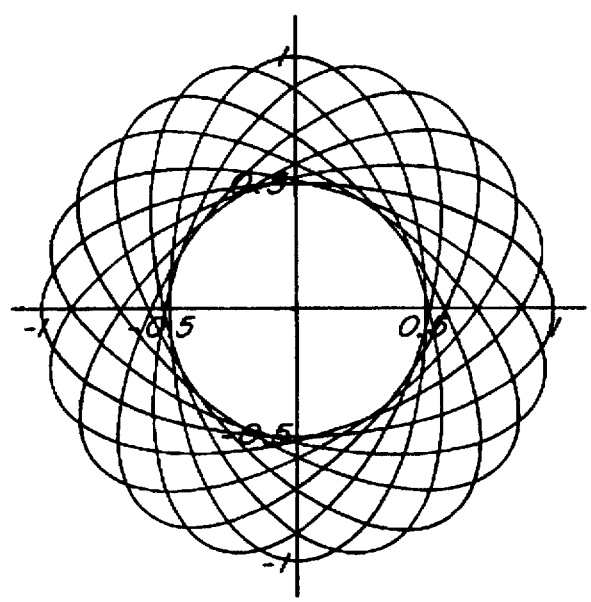
FIGS. 11–16 are computer generated plots of example rotating elliptical sensing patterns utilizing the teachings of the invention.
Figure 12:
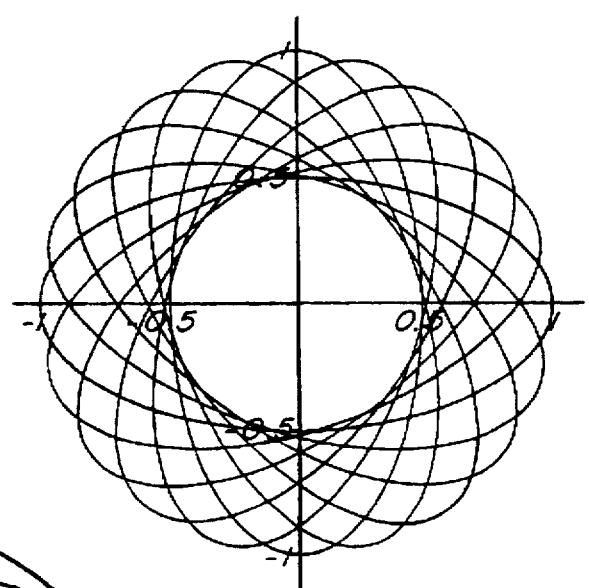
Figure 13:
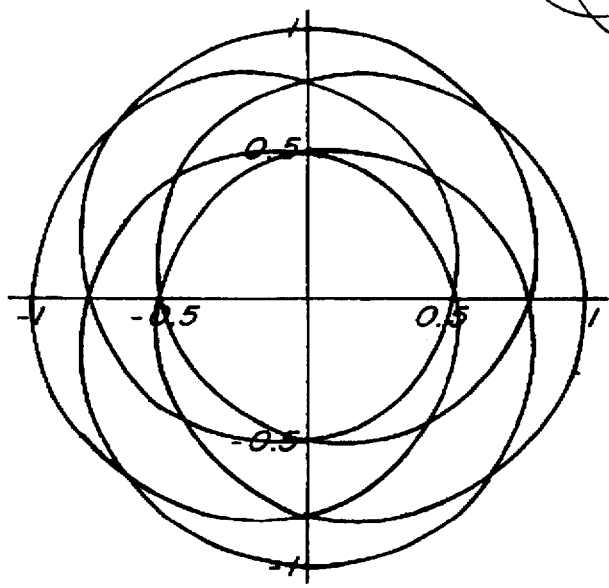
Figure 14:
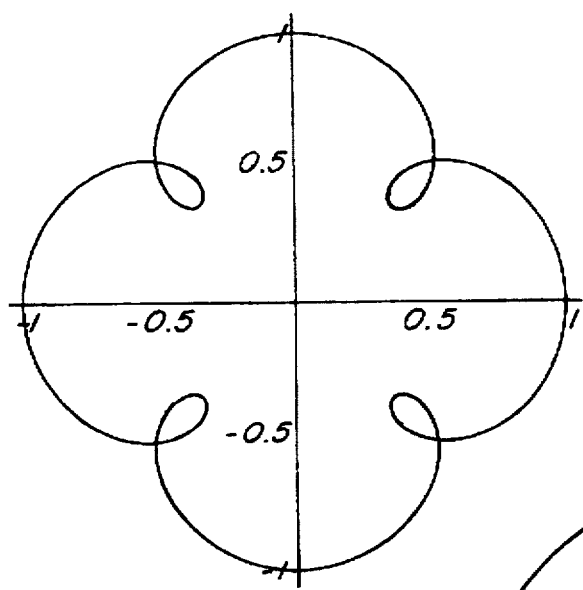
Figure 15:
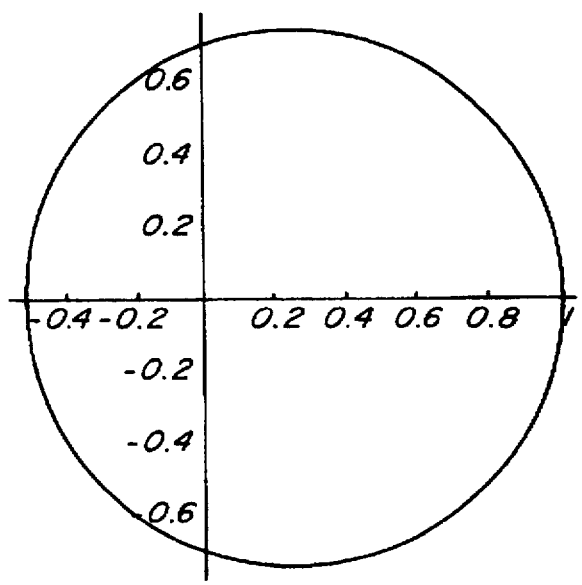
Figure 16:
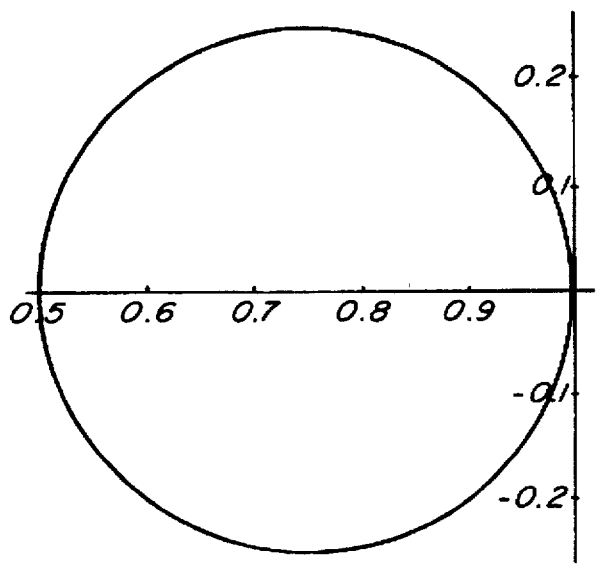

FIGS. 9 and 10 are oscilloscope pictures of actual prototype test waveforms of the output signal illustrating the amplitude and phase angle of the two signal components independent of the other. FIGS. 11–16 are computer generated x-y plots of example rotating elliptical sensing patterns that are possible utilizing suitable software. Careful examination of FIG. 11, shows the ellipse generation and the coordinate rotation (ellipse precession) are both rotating in the same direction. Examining FIG. 12, we see the ellipse generation is rotating in one direction i.e. cw and the ellipse precession is rotating ccw. The mathematical equations for generating this pattern are given above FIG. 12. FIGS. 13–16 are examples of various ratios of ellipse generation angular frequencies to coordinate rotation angular frequencies and also counter-rotational effects.

Each component of output signal should be processed for the phase angle and the amplitude level of each to extract workpiece characteristics.

I claim:

1. A method for generating and controlling a rotating elliptical sensing pattern for increasing the spatial resolution of a polar coordinate sensor coupled to a driving core having orthogonal windings fed by sine-cosine excitation waveforms, said method comprising the steps:

a) amplitude modulation of the said sine-cosine excitation waveforms by digital synthesis means; the said sensing pattern further comprising:
      i) an ellipse generation drawn with major and minor elliptical axes, generating a first angular frequency equal to the sine-cosine excitation frequency, the azimuth sensing range being intentionally reduced on the minor elliptical axis for spatial differentiation; and, ii) an ellipse precession comprising a plurality of individual ellipse generations drawn at different azimuth headings, the said ellipse precession generating a second angular frequency equal to a predetermined sub-multiple of the sine-cosine excitation frequency, the said sensing pattern subjecting a conducting work-piece to at least two induction frequencies for variable depth of eddy currents;

iii) down-loading a predetermined program into the said digital synthesis means for construction of the said sensing pattern.

2. The method as defined in claim 1, wherein the said predetermined program further comprises:

a) digital values for generating the said rotating elliptical sensing pattern in which the ellipse generation rotates in a positive direction at a first angular velocity and the ellipse precession rotates in a negative direction at a second angular velocity.

3. The method as defined in claim 1, wherein the said predetermined program further comprises:

a) digital values for generating the said rotating elliptical sensing pattern in which the ellipse generation and the ellipse precession rotate in the same direction at different angular velocities.

4. The method as defined in claim 1, wherein the said predetermined program further comprises:

a) digital values for generating the said rotating elliptical sensing pattern in which the ellipse generation rotates in a positive direction at a first angular velocity and the ellipse precession is drawn in a negative direction at a second angular velocity.

5. The method as defined in claim 1, wherein the said predetermined program further comprises:

a) digital values for generating the said rotating elliptical sensing pattern in which the degree of individual ellipse generations can be varied to change the length of the minor elliptical axis for selective spatial differentiation.

6. The method as defined in claim 1, wherein the said predetermined program further comprises:

a) digital values for generating the said rotating elliptical sensing pattern in which the sum of ellipse generations forming the sensing pattern are generated by a plurality of ellipse precession revolutions, individual ellipse generations having different azimuth headings for greater azimuth resolution.

7. The method as defined in claim 1, wherein the said predetermined program further comprises:

a) digital values for generating the said rotating elliptical sensing pattern in which a plurality of ellipse generations are generated in a positive angular direction (not necessarly a complete revolution) then a plurality of ellipse generations are generated in a negative angular direction but not necessarly at the former azimuth headings.

8. The method as defined in claim 1, wherein the said predetermined program further comprises:

a) digital values for generating the said rotating elliptical sensing pattern in which the ellipse precession advances to a first azimuth heading and then a plurality of ellipse generations are generated at the said first azimuth heading before the ellipse precession advances to subsequent azimuth headings for accumlative action.

9. The method as defined in claim 1, wherein the said predetermined program further comprises:

a) digital values for generating the said rotating elliptical sensing pattern in which the ellipse generation/ellipse precession ratio is made variable.

10. The method as defined in claim 1, wherein the said predetermined program further comprises:

a) a selection of different clock frequencies controlling the reading rate of the said digital values for different sensing pattern drawing velocities.

* * * * *